United States Patent [19]

Fitzpatrick

[11] Patent Number: 5,608,105
[45] Date of Patent: Mar. 4, 1997

[54] PRODUCTION OF LEVULINIC ACID FROM CARBOHYDRATE-CONTAINING MATERIALS

[75] Inventor: Stephen W. Fitzpatrick, Framingham, Mass.

[73] Assignee: Biofine Incorporated, Wilmington, Del.

[21] Appl. No.: 475,630

[22] Filed: Jun. 7, 1995

[51] Int. Cl.$^6$ .......................... C07C 51/00; C07C 307/48
[52] U.S. Cl. ........................... 562/515; 549/489; 549/490
[58] Field of Search ............................ 562/515; 549/489, 549/490

[56] References Cited

U.S. PATENT DOCUMENTS

| | | |
|---|---|---|
| 3,258,481 | 6/1966 | Sassenrath et al. . |
| 3,701,789 | 10/1972 | Ramos-Rodriguez . |
| 4,237,226 | 12/1980 | Grethlein . |
| 4,469,524 | 9/1984 | Assarsson et al. . |
| 4,497,896 | 2/1985 | Assarsson et al. . |
| 4,578,353 | 3/1986 | Assarsson et al. . |
| 4,897,497 | 1/1990 | Fitzpatrick .................. 562/515 X |

OTHER PUBLICATIONS

Thomas et al., "Biomass derived levulinic acid derivatives and their use as liquid fuel extenders", pp. 333–348, 1985.

Kwarteng, Abstract (Thayer School of Engineering), "Kinetics of acid hydrolysis of hardwood in a continuous plug flow reactor", (Jul. 1983).

*Primary Examiner*—Paul F. Shaver
*Attorney, Agent, or Firm*—Fish & Richardson P.C.

[57] ABSTRACT

A continuous process for producing levulinic acid from carbohydrate-containing materials in high yields is described. According to the process, a carbohydrate-containing material is supplied continuously to a first reactor and hydrolyzed at between 210° C. and 230° C. for between 13 seconds and 25 seconds in the presence of between 1% and 5% by weight mineral acid. The hydrolysis produces hydroxymethylfurfural, which is removed continuously from the first reactor and supplied continuously to a second reactor. In the second reactor, the hydroxymethylfurfural is hydrolyzed further at between 195° C. and 215° C. for between 15 minutes and 30 minutes to produce levulinic acid, which is continuously removed from the second reactor. The levulinic acid preferably is produced in at least 60%, and more preferably at least 70%, of the theoretical yield based on the hexose content of the carbohydrate-containing material.

17 Claims, 1 Drawing Sheet

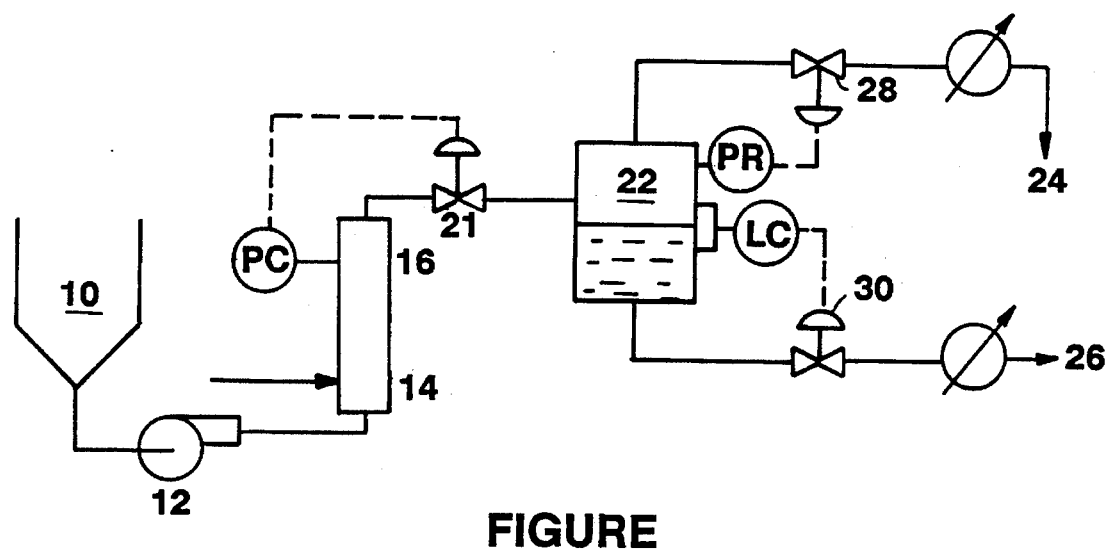
FIGURE

PRODUCTION OF LEVULINIC ACID FROM CARBOHYDRATE-CONTAINING MATERIALS

BACKGROUND OF THE INVENTION

This invention relates to the production of levulinic acid.

Many common materials consist partially or fully of carbohydrates. For example, cellulose and starch are polymers made of carbohydrate molecules, predominantly glucose, galactose, or similar hexoses. When subjected to acid treatment, cellulose and starch split into hexose monomers. On continued reaction the hexose monomers then further degrade to hydroxymethylfurfural, and other reaction intermediates, which then further degrade to levulinic acid and formic acid. Levulinic acid can be used to make resins, plasticizers, specialty chemicals, herbicides and a fuel extender, methyltetrahydrofuran.

Many common waste materials include cellulose or starch. For example, primary sludges from paper manufacture, waste paper, waste wood (e.g., sawdust), as well as agricultural residues such as corn husks, corn cobs, rice hulls, straw, and bagasse, include high percentages of cellulose. Starch can be found in food processing waste derived, for example, from corn, wheat oats, and barley.

SUMMARY OF THE INVENTION

The invention features a process for producing levulinic acid from carbohydrate-containing materials in high yields using two reactors in which the temperature, reaction time, and acid content are closely controlled. According to the preferred process, a carbohydrate-containing material is supplied continuously to a first reactor and hydrolyzed at between 210° C. and 230° C. for between 13 seconds and 25 seconds in the presence of between 1% and 5% by weight mineral acid. The hydrolysis produces hydroxymethylfurfural, which is removed continuously from the first reactor and supplied continuously to a second reactor. In the second reactor, the hydroxymethylfurfural is hydrolyzed further at between 195° C. and 215° C. for between 15 minutes and 30 minutes to produce levulinic acid, which is continuously removed from the second reactor. The levulinic acid preferably is produced in at least 60%, and more preferably at least 70%, of the theoretical yield based on the approximate hexose content of the carbohydrate-containing material.

The levulinic acid preferably is removed from the second reactor as it is generated by drawing off liquid containing the levulinic acid from the reactor. Solid by-products can be removed from the levulinic acid-containing liquid by filtration or centrifugation.

In preferred embodiments, the first reactor is a tubular reactor that includes an entrance and an exit between which the reactor mixture passes without significant axial mixing.

The contents of the second reactor are mixed either by an agitator or by allowing the outflow from the first reactor to enter the second reactor below the level of the liquid in the second reactor. This provides excellent mixing in the second reactor without the need for an agitator.

Preferably the flow of the intermediate sample is controlled by a flow valve that maintains steady conditions in the first reactor, and the volume of reactants in the second reactor is controlled by removing a volume corresponding to the volume fed to the second reactor. The latter may be accomplished by an outflow control valve which acts to maintain steady conditions such as mass level in the second reactor. The temperature in the second reactor preferably also is maintained constant, for example, by the injection of steam into the reactor, or by using a vapour outflow throttling valve which maintains a constant pressure in the second reactor.

Using a continuous two-stage reactor system in which the products are continuously collected provides an efficient use of equipment and space since large quantities of the sample can be run through a relatively small system and conditions in each stage of reaction can be precisely controlled. The lack of axial mixing in the first reactor ensures that a given portion of the sample does not spend too much time in the first reactor. The hydrolysis conditions—temperature, reaction time, and acid content—provide a surprisingly high yield of levulinic acid. In addition, the continuous nature of the second stage allows good control of conditions in the second stage.

Other features and advantages of the invention will be apparent from the description of the preferred embodiment thereof, and from the claims.

BRIEF DESCRIPTION OF THE DRAWING

The FIGURE is a flow diagram illustrating the steps of a preferred process.

DESCRIPTION OF THE PREFERRED EMBODIMENTS

Referring to the FIGURE, an aqueous acidified slurry 10 consisting of wastepaper fibers, paper sludge, sawdust, ground wood, ground corn, starch solution, or other carbohydrate feedstock in dilute mineral acid (e.g., sulfuric acid or hydrochloric acid) is pumped by a high pressure pump 12 into the entrance 14 of a tubular reactor 16. The acid may be premixed with the feed or injected by metering pump into the feedstream as it enters the first stage reactor. The temperature is maintained in the reactor at an elevated level by the injection of high pressure steam 18. The pressure in the reactor is maintained at a sufficient level to give rapid condensation of the steam and to prevent the reactor contents from vaporizing. The carbohydrate is degraded by the acid as the mixture passes through the reactor 16. The mixture flows in the axial direction along the reactor 16 such that the radial mixing is substantially greater than the axial mixing. The mixture flows out of the reactor through a variable orifice exit valve 21. The slurry may consist of 2% to 40% feed solids by weight; the quantity is limited only by the ability of the pump to feed the slurry.

While in the reactor 16 the carbohydrate material is degraded by the acid. Cellulose or starch, for example, in the feed degrade to hexose monomers and oligomers. Hemicellulose in the feed degrades to both hexose and pentose monomers and oligomers. The pentose monomers and oligomers are further degraded to furfural and the hexose monomers are further degraded to hydroxymethylfurfural.

The temperature in the first reactor preferably is 210° C. to 235° C. (more preferably 215° C. to °230 C.). If the temperature is too low, the acid degradation will not proceed at a fast enough rate. If the temperature is too high, too much pressure may be generate in the reactor and also, the first stage degradation may proceed too quickly.

The slurry preferably includes 1% to 5% (more preferably 1.5% to 3.5%) mineral acid by weight of the aqueous portion of the slurry. If too much acid is used, there may be corrosion problems with the equipment and the first stage degradation may proceed too quickly. If too little acid is used, the degradation may not proceed at a fast enough rate.

The amount of time the carbohydrate material spends in the reactor 16 should be about 13 seconds to 25 seconds (more preferably 13.5 seconds to 16 seconds). The material needs to have sufficient time to degrade, but the degradation products should not be exposed to elevated temperatures for an extended period or substantial unwanted decomposition of the products may occur.

The reaction mixture flows from reactor 16, through a pressure control valve 21, and into a tank-type reactor 22, which can be equipped with a stirrer to improve mixing. The temperature, mineral acid concentration, and average residence time of a volume of the mixture in the second reactor are selected so that the remaining hexose monomers, if any, are converted to hydroxymethylfurfural, and the hydroxymethylfurfural is further degraded to levulinic acid and any unreacted feed is converted to hexose which is then converted to levulinic acid. In addition, the conditions are adjusted so that any furfural and formic acid present vaporize quickly. The vapor 24 produced exits the reactor 22 and is externally condensed. The levulinic acid settles to the bottom of the reactor 22 with other liquids, and is continuously drawn off in liquid stream 26. For a given time period the volume removed from the reactor 22 should equal the volume of the reaction mixture added to the reactor 22 from the first reactor 16. Lignin or other solids leave the second reactor 22 in stream 26 and can be removed by filtration. Pressure control valve 28 and liquid pressure control valve 30 control the pressure in the reactor.

The temperature in the reactor 22 preferably should be 195° C. to 215° C. (more preferably 200° C. to 210° C.). If the temperature is too high substantial, unwanted, decomposition of the components of the mixture may occur and the reactor pressure may be too high. If the temperature is too low the conversion of hydroxymethylfurfural to levulinic acid may be too slow. The average residence time a given volume of the intermediate mixture from the first reactor remains in the reactor 22 should be 15 minutes to 30 minutes (more preferably 20 minutes to 30 minutes). Average residence time, as used herein, refers to the time it takes to remove from the reactor (by the draining of the liquid components such as levulinic acid) a volume of components of the mixture equal to the average volume of the mixture in the reactor 22. If the average residence time is too short, the degradation to the desired products may not be complete. If the average residence time is too long, the efficiency of the system may diminish.

The mineral acid concentration of the aqueous portion of the mixture in the reactor 22 preferably is 2% to 7.5%, preferably 3% to 7%, by weight. The mineral acid concentration can be adjusted upward at this stage, if desired, by adding acid to the mixture entering the reactor.

EXAMPLES

Examples 1–3 pertain to the conversion of a bleached kraft paper waste sludge to levulinic acid. The cellulose content of this sludge has been measured to be consistently in the range 42% to 50% by "Quansac" analysis (digestion by concentrated sulfuric acid). The average analysis is 44% by weight. That is, 100 lbs of bone dry sludge contains 44 lbs of cellulose which is available for conversion to levulinic acid.

Examples 4 and 5 pertain to conversion of a partially or non-bleached kraft paper sludge. The cellulose content of this sludge has been measured to be 80% by weight on average. That is, 100 lbs of bone dry sludge contains 80 lbs of cellulose which is available for conversion to levulinic acid. Example 6 pertains to conversion of raw wood flour. The cellulose content of this has been measured to be, on average, 42% by weight. That is, 100 lbs of bone dry sludge contains 42 lbs of cellulose which is available for conversion to levulinic acid.

Example 1

0.945 liters per minute of a 4.0% by weight slurry of paper sludge originating from a fully bleached Kraft pulping process containing 3.5% by weight of the aqueous portion sulfuric acid is fed to the reactor system. The first stage tubular reactor is fifteen feet in length and 0.41 inches in inside diameter. High pressure steam is injected into the process stream at an average rate of 0.47 liters per minute (condensed volume) as it passes into the tubular reactor. The residence time of the reaction mixture in the first stage tubular reactor is 14 seconds. The mixture passes through the pressure let-down valve and flashes directly into the second stage reactor vessel via the dip tube. The second stage reactor is a 10 inch I.D. (Schedule 20 pipe section) vessel of overall length 27 inches. The liquid level in the second stage is set by means of a load switch to give a second stage residence time of 30.0 minutes. The temperature in the first stage reactor was controlled at 232° C. by injection of high pressure steam. The pressure in the first stage reactor was controlled at between 450 and 476 pounds per square inch gauge by means of the pressure let-down valve at the end of the first stage reactor. The temperature in the second stage reactor was controlled at 196° C. and the pressure was controlled at between 207 and 210 psig by means of a vent throttle valve.

The liquid product outflow containing levulinic acid was measured at 1.276 liters per minute and the vent outflow was measured at 0.208 liters per minute after condensation. The levulinic acid concentration in the liquid outflow was measured by analysis to be 0.68% at steady state after four hours of operation. The product outflow from the reactor system was therefore calculated to be 0.0088 kg per minute representing a yield of levulinic acid of 76% of theoretical. A trace quantity (0.0001 kg per min) of levulinic acid was measured in the vent stream this was accounted for as additional yield.

Example 2

0.96 liters per minute of a 2.0% by weight slurry of paper sludge originating from a fully bleached Kraft pulping process containing 1.90% by weight of the aqueous portion sulfuric acid is fed to the reactor system. The first stage tubular reactor is fifteen feet in length and 0.41 inches in inside diameter. High pressure steam is injected into the process stream at an average rate of 0.47 liters per minute (condensed volume) as it passes into the tubular reactor. The residence time of the reaction mixture in the first stage tubular reactor is 14 seconds. The mixture passes through the pressure let-down valve and flashes directly into the second stage reactor vessel via the dip tube. The second stage reactor is a 10 inch I.D. (Schedule 20 pipe section) vessel of overall length 27 inches. The liquid level in the second stage is set by means of a load switch to give a second stage residence time of 20.0 minutes. The temperature in the first stage reactor was controlled at 215° C. by injection of high pressure steam. The pressure in the first stage reactor was controlled between 440 and 460 pounds per square inch gauge by means of the pressure let-down valve at the end of the first stage reactor. The temperature in the second stage reactor was controlled at between 200° and 205° C. and the pressure was controlled at between 230 and 255 psig by means of a vent throttle valve.

The liquid product outflow containing levulinic acid was measured at 1.28 liters per minute and the vent outflow was measured at 0.15 liters per minute after condensation. The levulinic acid concentration in the liquid outflow was measured by analysis to be 0.48% at steady state after four hours of operation. The product outflow from the reactor system was therefore calculated to be 0.0061 kg per minute representing a yield of levulinic acid of 86.7% of theoretical. No levulinic acid was measured in the vent stream.

Example 3

0.32 liters per minute of a 10% by weight slurry of paper sludge containing 3% by weight of the aqueous portion sulfuric acid is fed to the reactor system. The first stage tubular reactor is thirteen feet in length and 0.41 inches in inside diameter. High pressure steam is injected into the process stream at an average rate of 0.55 liters per minute (condensed volume) as it passes into the tubular reactor. The residence time of the reaction mixture in the first stage tubular reactor is 23.3 seconds. The mixture passes through the pressure let-down valve and flashes directly into the second stage reactor vessel via the dip tube. The second stage reactor is a 10 inch I.D. (Schedule 20 pipe section) vessel of overall length 27 inches. The liquid level in the second stage is set by means of a load switch to give a second stage residence time of 29.8 minutes. The temperature in the first stage reactor was controlled at 230° C. by injection of high pressure steam. The pressure in the first stage reactor was controlled between 440 and 460 pounds per square inch gauge by means of the pressure let-down valve at the end of the first stage reactor. The temperature in the second stage reactor was controlled between 206° and 210° C. and the pressure was controlled at between 230 and 255 psig by means of a vent throttle valve.

The liquid product outflow containing levulinic acid was measured at 0.530 liters per minute and the vent outflow was measured at 0.34 liters per minute after condensation. The levulinic acid concentration in the liquid outflow was measured by analysis to be 0.91% at steady state after two and a half hours of operation. The product outflow from the reactor system was therefore calculated to be 0.00482 kg per minute levulinic acid representing a yield of levulinic acid of 48.3% of theoretical. No levulinic acid was measured in the vent stream.

Example 4

1.02 liters per minute of a 1.0% by weight slurry of paper sludge originating from a non-bleached Kraft pulping process containing 1.15% by weight of the aqueous portion sulfuric acid is fed to the reactor system. The first stage tubular reaction is fifteen feet in length and 0.41 inches in inside diameter. High pressure steam is injected into the process stream at an average rate of 0.476 liters per minute (condensed volume) as it passes into the tubular reactor. The residence time of the reaction mixture in the first stage tubular reactor is 14 seconds. The mixture passes through the pressure let-down valve and flashes directly into the second stage reactor vessel via the dip tube. The second stage reactor is a 10 inch I.D. (Schedule 20 pipe section) vessel of overall length 27 inches. The liquid level in the second stage is set by means of a load switch to give a second stage residence time of 20.0 minutes. The temperature in the first stage reactor was controlled at 220° C. by injection of high pressure steam. The pressure in the first stage reactor was controlled at between 450 and 476 pounds per square inch gauge by means of the pressure let-down valve at the end of the first stage reactor. The temperature in the second stage reactor was controlled at 200° C. and the pressure was controlled at between 207 and 215 psig by means of a vent throttle valve.

The liquid product outflow containing levulinic acid was measured at 1.42 liters per minute and the vent outflow was measured at 0.076 liters per minute after condensation. The levulinic acid concentration in the liquid outflow was measured by analysis to be 0.36% at steady state after two hours of operation. The product outflow from the reactor system was therefore calculated to be 0.0073 kg per minute representing a yield of levulinic acid of 68% of theoretical. No levulinic acid was measured in the vent stream.

Example 5

1.04 liters per minute of 2.0% by weight slurry of paper sludge originating from a non-bleached Kraft pulping process containing 1.5% by weight of the aqueous portion sulfuric acid is fed to the reactor system. The first stage tubular reactor is fifteen feet in length and 0.41 inches in inside diameter. High pressure steam in injected into the process stream at an average rate of 0.32 liters per minute (condensed volume) as it passes into the tubular reactor. The residence time of the reaction mixture in the first stage tubular reactor is 14 seconds. The mixture passes through the pressure let-down valve and flashes directly into the second stage reactor vessel via the dip tube. The second stage reactor is a 10 I.D. (Schedule 20 pipe section) vessel of overall length 27 inches. The liquid level in the second stage is set by means of a load switch to give a second stage residence time of 25.0 minutes. The temperature in the first stage reactor was controlled at 215° C. by injection of high pressure steam. The pressure in the first stage reactor was controlled at between 450 and 476 pounds per square inch gauge by means of the pressure let-down valve at the end of the first stage reactor. The temperature in the second stage reactor was controlled at 200° C. and the pressure was controlled at between 207 and 215 psig by means of a vent throttle valve.

The liquid product outflow containing levulinic acid was measured at 1.34 liters per minute and the vent outflow was measured at 0.02 liters per minute after condensation. The levulinic acid and glucose concentration in the liquid outflow was measured at steady state after three and a half hours of operation. The yield of levulinic acid was calculated to be 71% of theoretical. No levulinic acid was measured in the vent stream.

After five hours of operation the feed to the system was reduced to 0.43 liters per minute and the second stage reactor allowed to react further with the reduced inflow and the temperature being maintained by injection of 0.22 liters per minute steam to the first stage. The yield of levulinic acid was found to increase to 92% of theoretical.

Example 6

0.70 liters per minute of a 10% by weight slurry of hardwood flour containing 5.0% by weight of the aqueous portion sulfuric acid is fed to the reactor system. The first stage tubular reactor is fifteen feet in length and 0.41 inches in inside diameter. High pressure steam is injected into the process stream at an average rate of 0.65 liters per minute (condensed volume) as it passes into the tubular reactor. The residence time of the reaction mixture in the first stage tubular reactor is 15.7 seconds. The mixture passes through the pressure let-down valve and flashes directly into the second stage reactor vessel via the dip tube. The second stage reactor is a 10 inch I.D. (Schedule 20 pipe section) vessel of overall length 27 inches. The liquid level in the second stage is set by means of a load switch to give a second stage residence time of 20.0 minutes. The temperature in the first stage reactor was controlled at 220° C. by injection of high pressure steam. The pressure in the first stage reactor was controlled by means of an orifice at the end of the first stage reactor. The temperature in the second stage reactor was controlled at 210° C. and the pressure was controlled by means of a vent throttle valve.

The liquid product outflow containing levulinic acid was measured at 1.15 liters per minute and the vent outflow was measured at 0.23 liters per minute after condensation. The levulinic acid concentration in the liquid outflow was measured by analysis to be 1.05% at steady state. The product outflow from the reactor system was therefore calculated to be 0.0121 kg per minute representing a yield of levulinic acid of 62% of theoretical. A small quantity (0.000069 Kg per min) of levulinic acid was measured in the vent stream this was accounted for as additional yield.

Other embodiments are within the claims. For example, other carbohydrate-containing materials like ground wood paper sludge and recycled paper sludge can be used in the process. Moreover, under some circumstances, such as in example 5, it may be improve yield if the second reactor is run as a batch process, instead of as a continuous process.

What is claimed is:

1. A continuous process for producing levulinic acid from a carbohydrate-containing material using a first reactor having an entrance and an exit and a second reactor having an entrance and an exit said process comprising, continuously supplying a sample containing said carbohydrate-containing material to said first reactor through said entrance to said first reactor, hydrolyzing said carbohydrate containing material in said first reactor at between 210° C. and 230° C. for between 13 seconds and 25 seconds in the presence of a mineral acid comprising between 1% and 5% by weight of said sample to produce hydroxymethylfurfural and other reaction intermediates, continuously removing an intermediate sample containing said hydroxymethylfurfural and other reaction intermediates from said first reactor through said exit of said first reactor in such a manner that substantially no axial mixing occurs in said first reactor, continuously supplying the intermediate sample that has been removed from said first reactor to said second reactor through said entrance to said second reactor, hydrolyzing said hydroxymethylfurfural and other reaction intermediates in said intermediate sample in said second reactor at between 195° C. and 215° C. for between 15 minutes and 30 minutes in the presence of a mineral acid comprising between 3% and 7.5% by weight of said intermediate sample to produce levulinic acid, and continuously removing levulinic acid from said second reactor through said exit of said second reactor, wherein the yield of levulinic acid removed from said second reactor comprises at least 60% of the theoretical yield.

2. The process of claim 1, wherein said carbohydrate-containing material is hydrolyzed in said first reactor at between 215° C. and 230° C.

3. The process of claim 1, wherein said carbohydrate-containing material is hydrolyzed in said first reactor for between 13.5 seconds and 16 seconds.

4. The process of claim 1, wherein in said first reactor said mineral acid comprises between 1.5% and 3.5% by weight of said sample.

5. The process of claim 1, wherein said hydroxymethylfurfural and other reaction intermediates are hydrolyzed in said second reactor at a temperature of between 200° C. and 210° C.

6. The process of claim 1, wherein said hydroxymethylfurfural and other reaction intermediates are hydrolyzed in said second reactor for between 20 seconds and 30 seconds.

7. The process of claim 1, wherein said carbohydrate-containing material is hydrolyzed in said first reactor at between 215° C. and 230° C. for between 13.5 seconds and 16 seconds in the presence of mineral acid comprising between 1.5% and 3.5% of said sample by weight, and wherein said hydroxymethylfurfural and other reaction intermediates are hydrolyzed in said second reactor at a temperature of between 200° C. and 210° C. for between 20 seconds and 30 seconds.

8. The process of claim 1 wherein said yield of levulinic acid is at least 70% of the theoretical yield.

9. The process of claim 1 wherein said carbohydrate-containing material comprises waste paper sludge.

10. The process of claim 9 wherein said waste paper sludge comprises bleached draft paper sludge.

11. The process of claim 9 wherein said waste paper sludge comprises unbleached draft paper sludge.

12. The process of claim 1 wherein said carbohydrate-containing material comprises raw wood flour.

13. The process of claim 1 wherein said entrance to said second reactor is below level of the liquid contents of said second reactor so that said intermediate sample entering said second reactor causes mixing of said liquid contents.

14. The process of claim 1 wherein glucose is a copendent of levulinic acid.

15. The process of claim 1 wherein said carbohydrate-containing material comprises recycled paper sludge.

16. The process of claim 1 wherein said carbohydrate-containing material comprises ground wood paper sludge.

17. The process of claim 1 wherein said carbohydrate-containing material consists essentially of cellulose-containing materials.

* * * * *

UNITED STATES PATENT AND TRADEMARK OFFICE
CERTIFICATE OF CORRECTION

PATENT NO. : 5,608,105
DATED : March 4, 1997
INVENTOR(S) : Stephen W. Fitzpatrick It is certified that error appears in the above-identified patent and that said Letters Patent is hereby corrected as shown below:

In col. 2, line 59, "°230" should be --230°--.

In col. 2, line 62, "generate" should be --generated--.

In col. 4, line 45, after "stream" insert --.--

In col. 4, line 45, "this" should be --This--.

In col. 6, line 29, "in" should be --is--.

In col. 7, line 27, after "stream" insert --.--

In col. 7, line 28, "this" should be --This--.

In the Figure, the number --18-- has been inserted (see attached amended formal drawing).

Signed and Sealed this

Twenty-eighth Day of July, 1998

Attest:

BRUCE LEHMAN

Attesting Officer

Commissioner of Patents and Trademarks

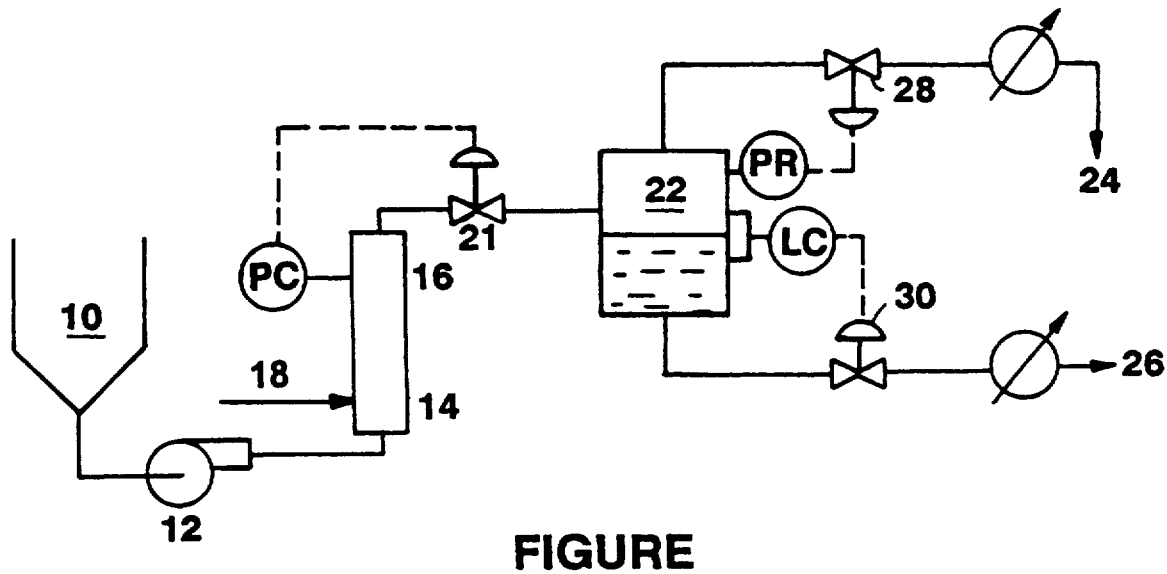
FIGURE